(12) United States Patent
Nakashima et al.

(10) Patent No.: US 7,947,290 B2
(45) Date of Patent: May 24, 2011

(54) PROTEASE-RESISTANT MODIFIED SEB AND VACCINE CONTAINING THE SAME

(75) Inventors: Toshihiro Nakashima, Kikuchi (JP); Takumi Sasaki, Kikuchi (JP); Tsukasa Nishihara, Kikuchi (JP); Sumiyo Takemoto, Kikuchi (JP); Atsuko Sakata, Kumamoto (JP); Masao Ohkuchi, Tokorozawa (JP); Tomoyuki Koshi, Shiki (JP); Toshiyuki Edano, Kawagoe (JP)

(73) Assignees: Juridical Foundation, The Chemo-Sero-Therapeutic Research Institute, Kumamoto-shi (JP); Kowa Company, Ltd., Nagoya-shi (JP)

( * ) Notice: Subject to any disclaimer, the term of this patent is extended or adjusted under 35 U.S.C. 154(b) by 0 days.

(21) Appl. No.: 12/644,952

(22) Filed: Dec. 22, 2009

(65) Prior Publication Data

US 2010/0166793 A1    Jul. 1, 2010

Related U.S. Application Data

(63) Continuation of application No. 10/570,499, filed as application No. PCT/JP2004/012545 on Aug. 31, 2004, now abandoned.

(30) Foreign Application Priority Data

Sep. 5, 2003   (JP) ................................. 2003-314187

(51) Int. Cl.
  *A61K 39/085*  (2006.01)
  *A61K 39/09*   (2006.01)
  *C07K 1/00*    (2006.01)
  *C07K 14/00*   (2006.01)
  *C07K 17/00*   (2006.01)

(52) U.S. Cl. .................. 424/243.1; 424/237.1; 530/350

(58) Field of Classification Search .................. 424/244, 424/236.1, 237.111; 530/350
See application file for complete search history.

(56) References Cited

U.S. PATENT DOCUMENTS 6,180,097 B1    1/2001  Terman
6,248,329 B1 *  6/2001  Chandrashekar et al. . 424/191.1

FOREIGN PATENT DOCUMENTS

| JP | 8-500328 A | | 1/1996 |
| JP | 1055429 A1 | * | 11/2000 |
| WO | WO93/14634 | * | 8/1993 |
| WO | 96/36366 A1 | | 11/1996 |
| WO | WO96/36366 | * | 11/1996 |
| WO | 99/40935 A | | 8/1999 |

OTHER PUBLICATIONS

Bowie et al (Science, 1990, 247:1306-1310).*
Ellis (Chapter 29 of Vaccines, Plotkin, et al. (eds) WB Saunders, Philadelphia, 1998, especially p. 571, paragraph 2).*
Ulrich et al In: R. ZChapter 31 Staphylococcal enterotoxin B and Related Pyrogenic Toxins R.G. In: R. Zatjchuk, Editor, Textbook of military medicine: Medical aspects of chemical and biological warfare Office of the Surgeon General, Department of Army, Washington, DC (1997), pp. 621-630.*
Savransky et al 2003 Toxicology Pathology vol. 31 pp. 373-378.*
Soos et al 1993 Neuroimmunol. vol. 43 (1-2) Abstract.*
A.C. Papageorgiou et al., Crystal structure of the superantigen enterotoxin C2 from Staphylococcus aureus reveals a zinc-binding site, Structure 2(8):769-779, (1995) XP004587900.
Savransky et al., Toxicology Pathology, 31:373-378 (2003).
Soos et al., Neuroimmunol., 43(1-2):39 (1993).
Ulrich et al., Chapter 31 Staphylococcal enterotoxin B and Related Pyrogenic toxins, 621-630, (1997).
Bowie et al., Science, 247:1306-1310 (1990).
Plotkin et al., Chapter 29 of Vaccines, (eds.) WB Sauders, Philadephia, 1998, especially p. 571, paragraph 2.

* cited by examiner

*Primary Examiner* — Robert A Zeman
*Assistant Examiner* — Nina A Archie
(74) *Attorney, Agent, or Firm* — Browdy and Neimark, PLLC

(57) ABSTRACT

A modified Staphylococcal enterotoxin B (SEB) having resistance to a protease and a reduced toxicity and a vaccine comprising said modified SEB are provided. A modified SEB which has an amino acid sequence as set forth in SEQ ID NO: 1 wherein each of the lysine at 97-position and the lysine at 98-position are substituted with any other amino acid, or a derivative thereof and a vaccine comprising said modified SEB or a derivative thereof.

1 Claim, 6 Drawing Sheets

PROTEASE-RESISTANT MODIFIED SEB AND VACCINE CONTAINING THE SAME

CROSS-REFERENCE TO RELATED APPLICATIONS

The present application is a continuation of application Ser. No. 10/570,499, filed Dec. 11, 2006, which is a 371 national stage application of PCT/JP04/12545, filed Aug. 31, 2004. The entire content of both applications are incorporated herein by reference.

TECHNICAL FIELD

The present invention relates to modified forms of Staphylococcal enterotoxin B (hereinafter also referred to as "SEB"), known as one of superantigens, or a derivative thereof and a vaccine comprising as an active ingredient the modified SEB or a derivative thereof and use of the vaccine. More particularly, the present invention relates to a modified SEB or a derivative thereof which has resistance to a protease and consequently has a reduced toxicity, and a vaccine comprising as an active ingredient said modified SEB or a derivative thereof and use of the vaccine.

BACKGROUND ART

SEB is one of enterotoxins (causative toxins of toxin-type food poisoning) produced by *Staphylococcus aureus*. SEB consists of 239 amino acid residues and its amino acid sequence is known (SEQ ID NO: 1). The SEB molecule comprises two domains, the first domain consisting of residues 1 to 120, and the second domain consisting of residues 127 to 239.

*Staphylococcus aureus* is indigenous bacteria. On the other hand, it is also known that infections caused by *Staphylococcus aureus* resistant to many antibiotics are extremely severe and have no good prognosis. Serious Staphylococcal infections, typically food poisoning, are mainly caused by toxins released out of the bacterial cells. Among such toxins, Staphylococcal enterotoxin (hereinafter also referred to as "SE") is a kind of superantigens and acts on a number of T lymphocytes to cause them to extensively produce inflammatory cytokines that would never occur under normal conditions (Non-patent reference 1). The action of extensive inflammatory cytokines causes shock-like symptoms which may lead the organism to death. It is reported that in healthy adults a proportion of those who possess an antibody to Staphylococcal enterotoxin (SE) becomes higher with age (Non-patent reference 2). Under immunodeficient conditions such as a terminal stage of malignant tumors, however, it is supposed that patients would be more likely to allow for invasion of drug-resistant *Staphylococcus aureus* to thereby undergo inflammation due to Staphylococcal enterotoxin B (SEB).

It is reported that a high proportion of atopic patients has an IgE type anti-SEB antibody and hence correlation between SEB and pathological conditions of atopic diseases is suspected (Non-patent reference 3).

Also, in case of rheumatoid patients, epidemiological data suggesting correlation between SEB and onset or pathological conditions of rheumatoid diseases are reported and association of an IgM type anti-SEB antibody with pathological conditions of rheumatoid diseases is reported (Non-patent reference 4).

Epidemiologically, it is reported that in human a proportion of those who possess an antibody against SEB increases with age with that of adults not less than 7 years old being almost 100% (Non-patent reference 5).

However, in general, an antibody titer of the antibody against SEB is not so high and it is not known whether said antibody has affinity sufficient for neutralization of SEB in blood.

On the other hand, for the purpose of prevention and treatment of various diseases associated with SEB such as food poisoning, there are many reports of modified SEB with decreased toxicity (Non-patent reference 6). The present inventors have also prepared modified SEB with much reduced toxicity and confirmed that said modified SEB maintained an ability to induce antibody production as SEB (SEB variant wherein the asparagine residue at 23-position is replaced with the tyrosine residue; Patent reference 1).

However, the conventional modified SEBs including those of the present inventors, though having a reduced toxicity, may still be able to activate human lymphocytes at a concentration of several ten ng/ml, which still needs be improved from the viewpoint of toxicity of a vaccine antigen.

There is a report on a modified SEB in which a contact region with MHC is modified, one in which a contact region with TCR is modified, and the like, based on conformational analysis of the SEB structure (Non-patent reference 7).

Patent reference 1: WO99/40935 pamphlet

Non-patent reference 1: v. v. Micusan and J. Thibodeau, "Seminars in Immunology", 1993, Vol. 5, p. 3-11

Non-patent reference 2: Kuwahata, M. et al., "Acta Pediatrica Japonica", 1996, 38, p. 1-7

Non-patent reference 3: Sohn M H., Kim G H, Kim W K, Jang G C, Kim K E, "Allergy Asthma Proc.", 2003, 24(1), p. 67-71

Non-patent reference 4: Origuchi T., Eguchi K., Kawabe Y., Yamashita I., Mizokami A., Ida H., Nagataki S., "Ann. Rheum. Dis.", 1995, 54(9), p. 713-720

Non-patent reference 5: Kuwahata, M., Imanaka, H., Takei, S, and Masuda, K., "Acta Oediatrica Japonica", 1996, 38, p. 1-7

Non-patent reference 6: Woody M A, Krakauer T, Stiles B G, "Vaccine", 1997, 15(2), p. 133-139

Non-patent reference 7: Leder L. et al., "Journal of Experimental Medicine", 1998, 187(6), p. 823-833

DISCLOSURE OF THE INVENTION

Technical Problem to be Solved by the Invention

However, reduction in toxicity of the conventional modified SEBs is insufficient as described above and simple mutation at a contact region in SEB was thought to have limitation.

Means for Solving the Problems

The present inventors have earnestly studied the effects of SEB amino acid mutation on its activity and as a consequence focused on relationship between mutation at a protease cleavage site and manifestation of toxicity.

There are in total 37 sites for trypsin recognition sequence on the linear sequence of wild type SEB. Among these, however, it is only at the C-terminal of the lysine at 97-position, the lysine at 98-position, and at the C-terminal of the lysine at 238-position, the lysine at 239-position that actual cleavage may occur under neutral buffer condition similar to within the normal living body as experimentally proved.

It was found however that cleavage of these sites would not affect the activity of SEB (i.e. activity to activate and to proliferate lymphocytes) nor alter reactivity of SEB with an anti-SEB antibody.

Within the intestinal tract, SEB is likely to be in such a cleaved form as described above by the action of trypsin derived from the pancreas to thereby exert the activity.

On the other hand, a human anti-SEB antibody includes plural antibodies against linear epitopes as revealed by e.g. Western blot analysis, suggesting that SEB not only acts as superantigens but also is subject to processing by antigen-presenting cells for antigen presentation. Thus, mutation at the protease cleavage sites may possibly alter the antibody-inducing ability of SEB.

Based on the intelligence and the analytical results as described above, the present inventors have focused on the lysine at 97-position and the lysine at 98-position. Structurally, these two amino acids are present on a loop connecting the N-terminal domain and the C-terminal domain of SEB. There is possibility that motion and cleavage of this loop may largely be involved in structural alteration associated with manifestation of the SEB activity. Besides, the present inventors have also found that this site is not only cleaved by trypsin but also by cathepsin B.

Cathepsin B is an enzyme known to be deeply involved in antigen processing within the antigen-presenting cells. It is thus expected that introduction of mutation at this site may greatly affect dynamism of SEB within the living body, antigen presentation and manifestation of toxicity.

Thus, using the genetic engineering technique, the present inventors have prepared plural SEB mutants by further introducing mutation at the lysine at 97-position and the lysine at 98-position in the amino acid sequence of a modified SEB in which the asparagine at 23-position has been replaced with tyrosine and let the mutants expressed in E. coli. As a result, a modified SEB in which both the lysine at 97-position and the lysine at 98-position were replaced with serine ("N23YK97SK918S") exhibited an excellent expression level. Designation in connection with modification of SEB as used herein is such that names of amino acid before and after modification are placed before and after the numeral of a certain amino acid residue, respectively. For instance, "N23Y" means a modified SEB in which "N" (Asn: asparagine) at the 23rd (23-position) amino acid counted from the N-terminal is replaced with "Y" (Tyr: tyrosine). In case of a modified SEB in which two or more amino acid residues are replaced, each designation of respective modified amino acids are consecutively set forth in tandem [For instance, "N23YK97SK98S" means a modified SEB in which "N" (Asn: asparagine) at the 23rd (23-position) amino acid counted from the N-terminal is replaced with "Y" (Tyr: tyrosine), and "K" (Lys: lysine) at the 97th (97-position) and at the 98th (98-position) are replaced with serine, respectively]. The amino acid sequence of "N23YK97SK98S" modified SEB is set forth in SEQ ID NO: 2.

More Efficacious Effects than Prior Art

As expected, this modified SEB, after purification, showed on one hand resistance to trypsin or cathepsin B treatment and on the other hand possessed sufficient reactivity with an anti-SEB antibody with its antigenicity as SEB being much the same as that of natural SEB.

It was thus proved that the lymphocyte-proliferating activity and the cytokine production-inducing activity could drastically be reduced by further modifying the two lysine residues at 97- and 98-positions in addition to mutation of asparagine at 23-position to tyrosine ("N23Y" modified SEB). In particular, the lymphocyte-proliferating activity of "N23YK97SK98S" modified SEB in accordance with the present invention had been much reduced to one to a million as compared to natural SEB or to around one to ten thousand relative to "N23Y" modified SEB.

Besides, the "N23YK97SK98S" modified SEB of the present invention had also the cytokine production-inducing activity much reduced as compared to natural SEB, e.g. with no induction of inflammatory cytokines except for IL-4 which was about 40% of natural SEB, and hence was effective in reduction of the activity. Some of the toxicities by SEB are thought to be caused by monokines, especially tumor necrosis factor-α (TNF-α), produced by leukocytes stimulated by SEB. Accordingly, decrease in the lymphocyte-proliferating activity and the cytokine production-inducing activity may be an index of reduction in SEB toxicity.

When the "N23YK97SK98S" modified SEB of the present invention was injected intraperitoneally to mice together with adjuvant for immunization in a conventional manner, an antibody with a significantly higher antibody titer than that of the "N23Y" modified SEB could be induced, said antibody being of the same property as that of one produced when mice were immunized with the "N23Y" modified SEB.

BRIEF DESCRIPTION OF DRAWINGS

FIG. 1 shows the results of SDS-PAGE for fragments obtained after trypsinization of the "N23Y" modified SEB and the "N23YK97SK98S" modified SEB of the present invention. T: Trypsinization, M: Molecular weight standard.

FIG. 2 is a graph showing a distribution of an antibody titer of an anti-SEB antibody after inoculation of the purified "N23Y" modified SEB or "N23YK97SK98S" modified SEB of the present invention into BALE/c mice.

FIG. 3 is a graph showing reactivity of an antiserum obtained by immunization with the "N23YK97SK98S" modified SEB of the present invention in comparison with reactivity of an antiserum obtained by immunization with the "N23Y" modified SEB.

FIG. 5 is a graph showing a blast formation-stimulating activity of the "N23YK97SK98S" modified SEB of the present invention in comparison with those of wild type SEB and of the "N23Y" modified SEB.

BEST MODE FOR CARRYING OUT THE INVENTION

Figure 4:
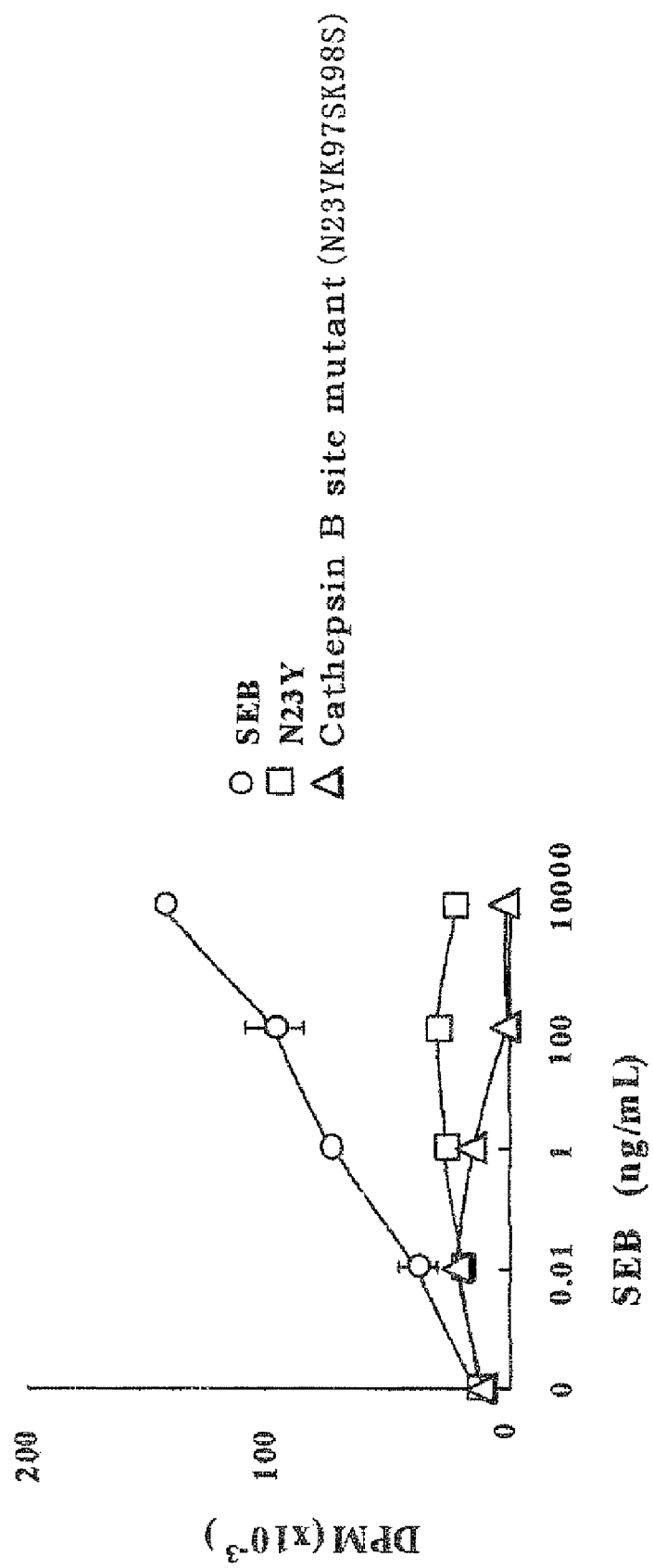
FIG. 4 is a graph showing a cell proliferation-stimulating activity of the "N23YK97SK98S" modified SEB of the present invention in comparison with those of wild type SEB and of the "N23Y" modified SEB.

As a basis of the modified SEB according to the present invention, wild type SEB (SEB prepared by the genetic engineering technique having the same amino acid sequence as that of SEB derived from Staphylococcus aureus) may be prepared e.g. in a manner as described below.

Since the sequence of the chromosomal DNAs of SEB is known (Ranelli D. M. et al., Proc. Natl. Acad. Sci. USA., Vol. 82, p. 5850-(1985)), a 5' sense primer and a 3' antisense primer may be synthesized with a DNA synthesizer. With these primers and the chromosomal DNAs present in a commercially available DNA library of Staphylococcus aureus, plaque hybridization is performed to select plaques. Then, PCR is performed with the sense primer and DNAs are extracted from the band obtained. The extracted DNAs are inserted into a suitable cloning vector for cloning.

A cloned gene encoding SEB is cleaved with restriction enzymes such as Sad, HindIII, EcoRI, BamHI, XbaI, SalI and PstI and the cleaved fragments are incorporated into a vector similarly cleaved with the restriction enzymes such as XmnI, HindIII, EcoRI, BamHI, XbaI, SalI and PstI to obtain a recombinant DNA (Sambrook et al., Molecular Cloning, 2nd ed., Chap. 9, 1989, New York, Cold Spring Harbor Laboratory Press). As a vector for this purpose, a secretionary expression vector such as pTrc99A may suitably be used.

The obtained recombinant DNA may be incorporated into a suitable host, e.g. *E. coli*, to generate a transformant. The transformant may be cultured in a conventional manner. Upon completion of culture, the cells may be removed and disrupted in a conventional manner and a desired wild type SEB may be obtained from the suspension. According to conditions, however, a wild type SEB may suitably be secreted into culture supernatant to allow for the culture supernatant be used as a starting material. The starting material is then subject to purification with a purifying means such as immunoaffinity chromatography in which an anti-SEB monoclonal antibody is bound to an adsorbent. A buffer used for final preparation in each test may preferably include Tris-HCl buffer, phosphate buffer, and the like.

A modified SEB of the present invention may be prepared in the same manner as described above for the preparation of wild type SEB.

For maintaining the prepared wild type SEB and the modified SEB to the maximum degree, it may either be fresh or preferably used within about five days after storage at 4° C. Alternatively, the modified SEB of the present invention may be stored under suitable circumstances such as gelatin, salts, sugars, sugar alcohols or amino acids.

Besides, in accordance with the present invention, the modified SEB as an active ingredient may be combined with a suitable known excipient to thereby formulate a vaccine preparation of the present invention by the known method. For a final dosage form of the vaccine preparation, powder (solid), liquid or syrup may be envisaged that may be applicable for subcutaneous, intramuscular or oral administration. For instance, in preferable embodiments, the modified SEB alone, or in combination with an adjuvant such as aluminum adjuvant, may be lyophilized together with a suitable excipient, e.g. carbohydrates, sugars, sugar alcohols or amino acids, to formulate into a solid preparation, or the modified SEB may be dissolved in a saline and a suitable buffer with acceptable ionic strength to formulate into a liquid preparation. Alternatively, the modified SEB as an active ingredient may be dissolved in commercially available beverage for oral supply. A content of the modified SEB in the preparation may be in a range of from 0.1 µg to 100 mg (0.002 to 2 mg/Kg body weight) per administration, preferably from 1 µg to 5 mg (0.02 µg to 100 µg/Kg body weight).

An effective dose of a vaccine preparation comprising as an active ingredient the modified SEB or a derivative thereof according to the present invention may vary depending on e.g. the age of patients to be administered, symptoms and severity of disease and ultimately be left to physician's discretion. It may be however in a range of from 0.1 µg/day to 1 mg/day for adult on the basis of an amount of the modified SEB and preferably a dose in a range of from 0.1 µg to 5 mg may be administered at a time or in two portions. As the occasion demands, the vaccine preparation of the present invention may be applied in combination with other medicaments such as steroids.

A "derivative" of the modified SEB of the present invention as used herein refers to the modified SEB, having at least one amino acid substitution as described above, that further underwent additional amino acid modification. Thus, the derivative of the modified SEB of the present invention encompasses the modified SEB that, in addition to the specific amino acid substitutions as described above, has additional amino acid substitution, deletion or insertion in any of the amino acid residues in the amino acid sequence of natural SEB and still has the activity equivalent to that of the modified SEB of the present invention.

EXAMPLES

The present invention is explained in more detail by means of the following Preparation and Examples but should not be construed to be limited thereto.

Preparation 1

Preparation and Expression of Recombinant Modified SEB 1-1: Cloning of SEB Gene

A DNA library of *Staphylococcus aureus* enterotoxin A+B+C was purchased from CLONOTEC and plaque hybridization was performed. Antisense synthetic DNAs or PCR fragments were used as a probe. For facilitating the subsequent cloning, SalI cleavage sites were introduced at both ends of the primers.

Plaques bound with the above primers were selected and subject to PCR with sense primers. DNAs were extracted from the bands obtained and cloned into PCR-II vector (Invitrogen). Table 1 shows the primers used for hybridization as described above.

TABLE 1

Antisense:

5'-AAG TCG ACA ATA TTA GAA AAG GCA GGT ACT-3'  (SEQ ID NO: 3)
    Sal I

Sense:

5'-ATG TCG ACT TAA TTG AAT ATT TAA GAT TAT-3'  (SEQ ID NO: 4)
    Sal I

Then, a nucleotide sequence of the DNA was determined with an automated sequencer. The obtained SEB gene was found to contain a promoter region (SEB-Pro). Thus, in order to obtain an SEB gene that does not contain a promoter region, PCR was further performed with the primers described in Table 2 and the obtained DNA fragments were cloned into PCR-II vector.

TABLE 2

Sense:

5'-AAG TCG ACA AAA AAT GTA TAA GAG ATT ATT-3'  (SEQ ID NO: 5)
       Sal I

Antisense:

5'-AAG TCG ACT TTC ACT TTT TCT TTG TCG TAA-3'  (SEQ ID NO: 6)
       Sal I

For the obtained SEB gene, a nucleotide sequence of the DNA was determined with the automated sequencer to reveal that said SEB gene did not contain any mutation. The SEB gene that does not contain a promoter region was cleaved with SalI and cloned into a secretionary expression vector pTrc99A (Pharmacia Biotech) that has the same cleavage site. Those with insertion in correct orientation were subject to induction with IPTG to confirm that SEB could be expressed and secreted.

1-2: Polymerase Chain Reaction (PCR)

In this Example, PCR was performed with Taq polymerase and a DNA Circle Cycler from Perkin Elmer Cetus (Norwalk, Conn., USA) as reported by Saiki et al. (Science vol. 239, p. 487, 1988). Processes of denaturing (94° C., 1 minute) for denature and dissociation of double-stranded template DNAs, annealing (55° C., 2 minutes) for associating the primers and the template, and elongation (72° C., 2 minutes) for synthesis were repeated for 30 to 35 cycles. A concentration was 1 nM to 1 µM for the template and 1 mM for the oligonucleotide primers.

1-3: Preparation and Expression of Recombinant Modified SEB

Only such modified SEBs that introduced amino acid substitution were expressed recombinationally. Table 3 shows the site of introduction of amino acid substitution.

TABLE 3

| Modified position(s) | Change | Designation |
|---|---|---|
| N23 | Asn→ Tyr | N23Y |
| N23, K97, K98 | Asn→ Tyr, Lys→ Ser, Lys→ Ser | N23Y K97S K98S |

1-4: Introduction of Amino Acid Substitution

Using as a template a plasmid pTrc99A/N23Y in which N23Y (SEB mutant with the asparagine at 23-position being replaced with tyrosine; International Application PCT/JP99/00638), one of modified SEBs, was incorporated into pTrc99A, PCR was performed using PCR primers with mutation in their nucleotide sequences allowing for change in the amino acids at 97- and 98-positions into desired amino acids to prepare modified SEBs. Mutagenesis was done as described below.

A 5' primer and a 3' primer (antisense) were synthesized that corresponded to the 5'-terminal of SEB in pTrc99A/N23Y with addition of SfiI sequence and to the 3'-terminal of SEB with addition of NatI sequence, respectively. Besides, for change in the amino acids at 97- and 98-positions, K97SK98S sense and antisense primers were synthesized.

```
K97SK98S sense primer
                                        (SEQ ID NO: 7)
CAATGTTATTTTTCTAGCAGCACGAATGATATTAATTCGCAT
```

```
K97SK98S antisense primer
                                        (SEQ ID NO: 8)
ATGCGAATTAATATCATTCGTGCTGCTAGAAAAATAACATTG
```

Using pTrc99A/N23Y as a template, the 5 primer and the K97SK98S antisense primer were used for amplification of a 5' region containing the mutation whereas the K97SK98S sense primer and the 3' primer were used for amplification of a 3' region containing the mutation, in PCR.

Assembly PCR was performed using the obtained two DNA fragments to prepare a full-length mutant N23YK97SK98S DNA. This full-length DNA fragment was cloned into pTrc99A. The cloned N23YK97SK98S modified SEB was sequenced for its nucleotide sequence so as to confirm if mutagenesis was correctly introduced.

1-5: Expression of Modified SEB and Preparation of Said Modified SEB

The modified SEB was expressed with the modified SEB gene inserted into pTrc99A vector. E. coli cells with the incorporated gene were cultured in a culture medium containing 4% CIRCLEGROW (BIO 101 Inc., Vista, Calif., USA) and ampicillin (50 mg/ml) at 37° C. for 18 hours. The cells were collected and suspended in the same culture medium at O.D. 550 nm of 0.3 to 1.0. 2 mM Isopropyl-B-D(−)-thiogalactopyranoside (IPTG) was added and the culture was shook at 37° C. overnight for induction. After induction, the host E. coli cells were removed by centrifugation and the culture supernatant was filtered through 0.45 µm filter membrane.

The thus prepared culture supernatant was passed through Sepharose 4B column immobilized with an anti-SEB monoclonal antibody SA58-2-6IgG to thereby adsorb the modified SEB contained in the culture supernatant. After the column was washed with 0.1M Tris-HCl (pH 8.0), the modified SEB was eluted with 4M MgCl$_2$. The eluted fractions were dialyzed against a 20-fold volume of saline thrice and against a 20-fold volume of PBS twice. The modified SEB in accordance with the present invention could all be purified with this monoclonal antibody column.

Example 1

Lethal Toxicity Test with Mice

As reported by Miethke T. et al., it is known that although no lethal toxicity would normally be brought about with natural SEB in mice, administration of 20 µg/kg D-galactosamine followed by intravenous or intraperitoneal administration of 20 µg/mouse SEB would lead to death in mice (J. Exp. Med., Vol. 175, p. 91-98 (1992)). In this Example, whether the modified SEB may indeed be improved in lethality in mice was investigated by administering SEB or the modified SEB to mice which previously received D-galactosamine.

First, in order to assess susceptibility to endotoxin, 20 mg/mouse of D-galactosamine was administered to BALB/c mice and then LPS (lipopolysaccharide) from *E. coli* B4 was administered intravenously to investigate lethality after 24 hours. As a result, it was found that an LPS dose of 1 ng/mice or less lead to no death of animal (Table 4).

TABLE 4

| Dose | Number of Death/Total number |
|---|---|
| 1 µg/head | 7/9 |
| 100 ng/head | 8/9 |
| 10 ng/head | 5/9 |
| 1 ng/head | 0/9 |
| 0.1 ng/head | 0/9 |

Endotoxin contained in a sample of the modified SEB was removed to a final dose of 10 ng/mouse or less and the experiment was performed with male mice. Since lethal toxicity of SEB after administration of D-galactosamine was manifested with 100 µg/mouse or more in male mice, a dose of the modified SEB was determined to be 100 µg/mouse. As shown in Table 5, natural SEB and wild type SEB showed high lethality to indicate their lethal toxicity whereas the modified SEBs had a reduced lethal toxicity. The term "natural SEB" as used herein means enterotoxin derived from *Staphylococcus aureus* and the term "wild type SEB" means SEB prepared by the genetic recombination technique that has the same amino acid sequence as that of natural SEB.

TABLE 5

| | Lethality (Total number of death/Total number) after | |
|---|---|---|
| Modified SEB (100 µg/head) | 24 hours | 48 hours |
| Natural SEB | 8/10 | 8/10 |
| Wild type SEB | 7/10 | 9/10 |
| N23Y | 0/10 | 0/10 |
| N23YK97SK98S | 0/10 | 0/10 |
| PBS | 0/10 | 0/10 |

Next, the similar experiment was repeated with female BALB/c mice. In female mice, a high lethal toxicity was observed with 20 µg/mouse of SEB when 40 mg/mice of D-galactosamine was administered. It was found that natural SEB and wild type SEB showed a high lethality whereas the modified SEBs had a lowered lethality and hence a reduced lethal toxicity.

Example 2

Protease Resistance of Modified SEB

Figures 1, 2:
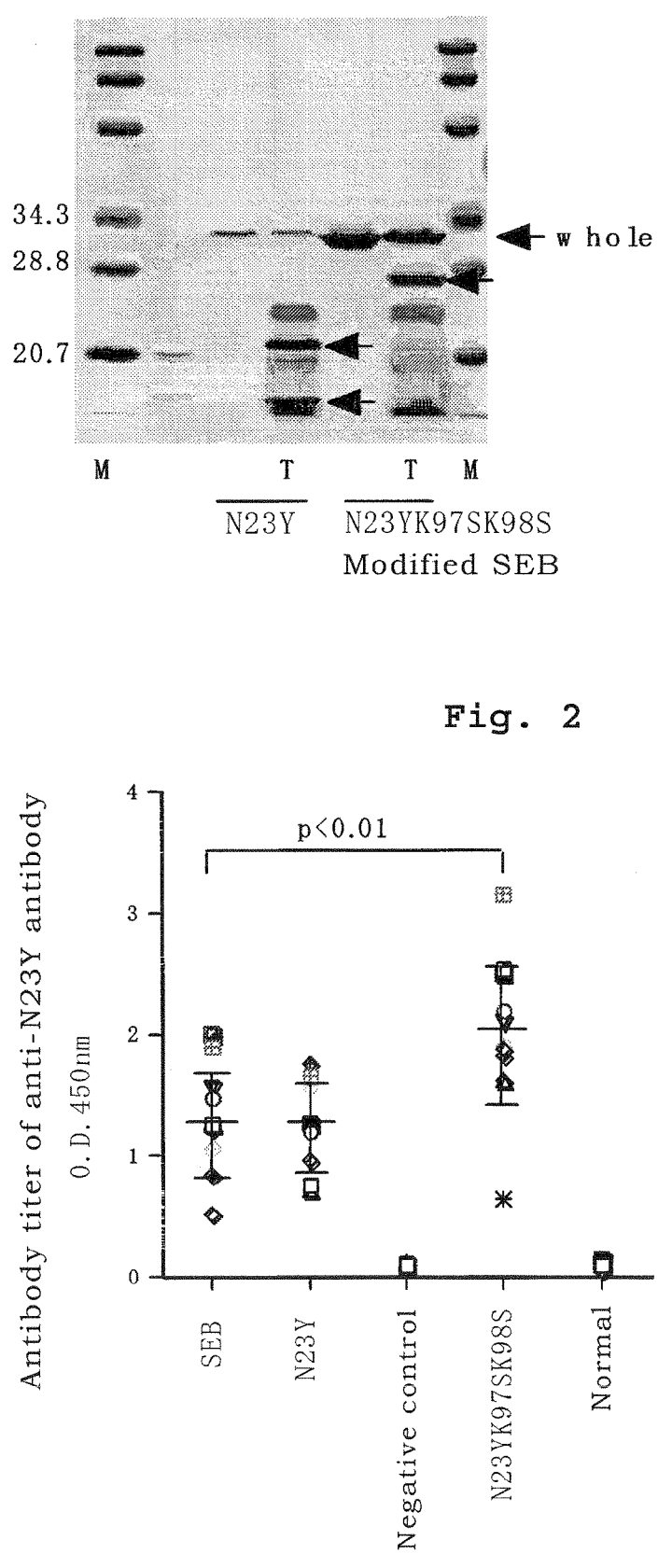

To each 100 µg/ml (500 µl) of the purified modified SEBs N23Y and N23YK97SK98S dissolved in phosphate buffered saline (PBS, pH 7.2) was added 10 µg of trypsin for reaction at 37° C. for 1 hour. One mg of trypsin inhibitor was added to the mixture to quench the reaction and 20 µl of the solution was removed and analyzed for reaction products by SDS-PAGE. As a result, the modified SEB N23Y was cleaved into two fragments, i.e. C-terminal (around 21 Kda) and N-terminal (around 10 Kda), whereas two bands at the same position as that before digestion (around 32 Kda) and at around 28 Kda were observed for the modified SEB N23YK97SK98S. Western blot analysis confirmed that these bands were reactive with an anti-SEB antibody (FIG. 1). Besides, N-terminal analysis indicated that these two bands had the same N-terminal sequence as that of SEB. It was thus estimated that the band at around 28 Kda was the modified SEB N23YK97SK98S in which the C-terminal lysine was removed through trypsin digestion to thereby render basicity of the modified SEB reduced so that the modified SEB is electrophoresed at the vicinity of theoretical value (28.3 Kda).

Therefore, the modified SEB N23YK97SK98S would not be cleaved with trypsin other than at the position described above and thus was confirmed to have enough resistance to a serine protease. Likewise, the modified SEB N23YK97SK98S behaved similarly to cathepsin B and thus was proved to have resistance to cathepsin B.

Example 3

Immunological Experiment of Modified SEB

An emulsion of 20 µg of the purified modified SEB N23YK97SK98S or N23Y with FCA was inoculated intraperitoneally to BALB/c mice of 3 to 4 weeks old (female). An endotoxin content of the purified modified SEBs N23YK97SK98S and N23Y was 0.05 EU/mg or less.

After 2 weeks, mice were bled and an antibody titer of an anti-SEB antibody in blood was determined by ELISA. FIG. 2 shows a distribution of an antibody titer of an anti-SEB antibody in each mouse after dilution by 10,000-fold. It was demonstrated that the group immunized with the modified SEB N23YK97SK98S had a significantly enhanced antibody titer of an anti-SEB antibody in blood as compared to that of the group immunized with N23Y.

Figure 3:
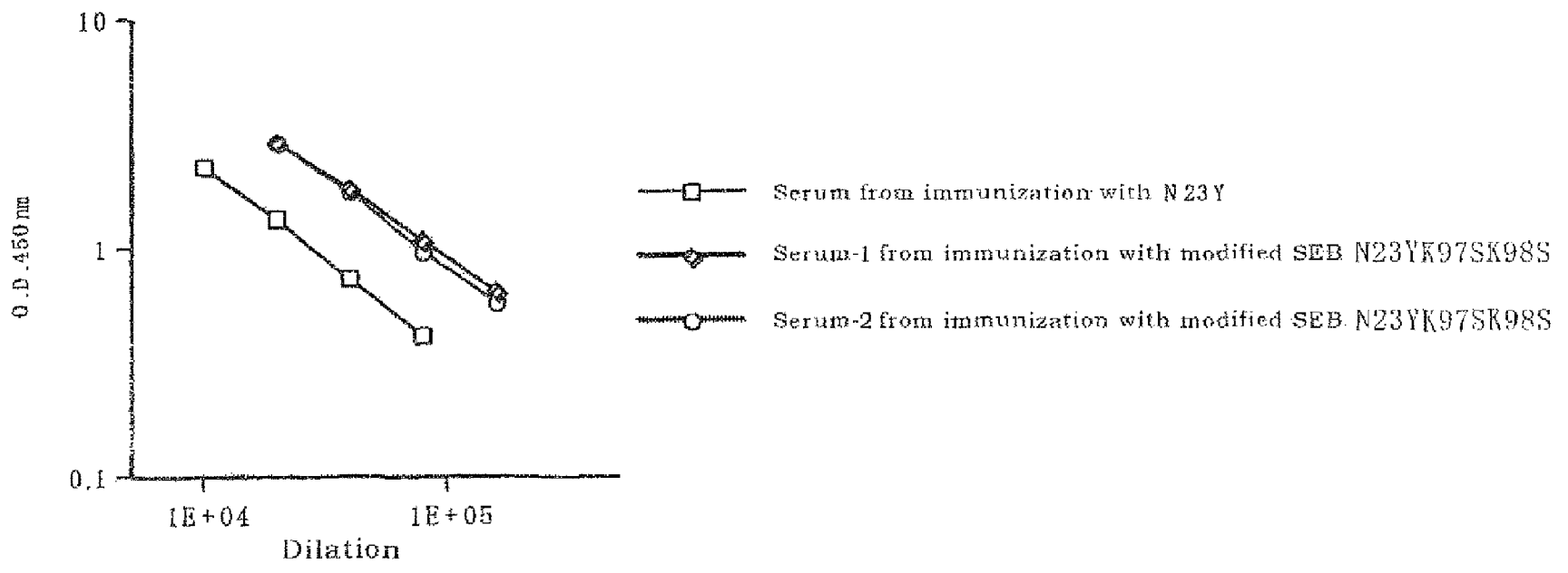

A property of an antibody produced by the modified SEB N23YK97SK98S was compared with that of an antiserum obtained by immunization with wild type SEB or the modified SEB N23Y. As a result, it was found that an antibody produced by the modified SEB N23YK97SK98S showed similar reactivity with wild type SEB and thus was proved to be qualitatively equivalent to an antiserum obtained by immunization with wild type SEB or the modified SEB N23Y and to have well enough a neutralizing activity (FIG. 3).

Example 4

Assessment of Lymphocyte-Proliferating Activity and Blast Formation-Inducing Activity of Modified SEB Peripheral blood mononuclear cells (hereinafter also referred to as "PBMCs") from healthy adults were inoculated to a 96-well plate at $1 \times 10^5$ cells/well and stimulated with SEB, the modified SEB N23Y or N23YK97SK98S at a concentration of 0.01, 1, 100 or 10000 ng/mL for 3 days. Sixteen hours before harvest, the stimulated PBMCs were let to take in tritium-thymidine (0.5 µCi) and a proliferation-inducing activity was investigated. As a result, as shown in FIG. 4, SEB exhibited a potent proliferation-inducing activity to PBMCs at 0.01 ng/mL or more in a concentration dependent manner. N23Y had a considerably weaker proliferation-inducing activity than that of SEB wherein a take-in of tritium-thymidine began to be detected at 100 ng/mL or more and a count at 10000 ng/mL was about 1/10 of SEB. The modified SEB N23YK97SK98S had a further reduced proliferation-stimulating activity with almost no take-in of tritium-thymidine even at 10000 ng/mL (FIG. 4).

Figure 5:
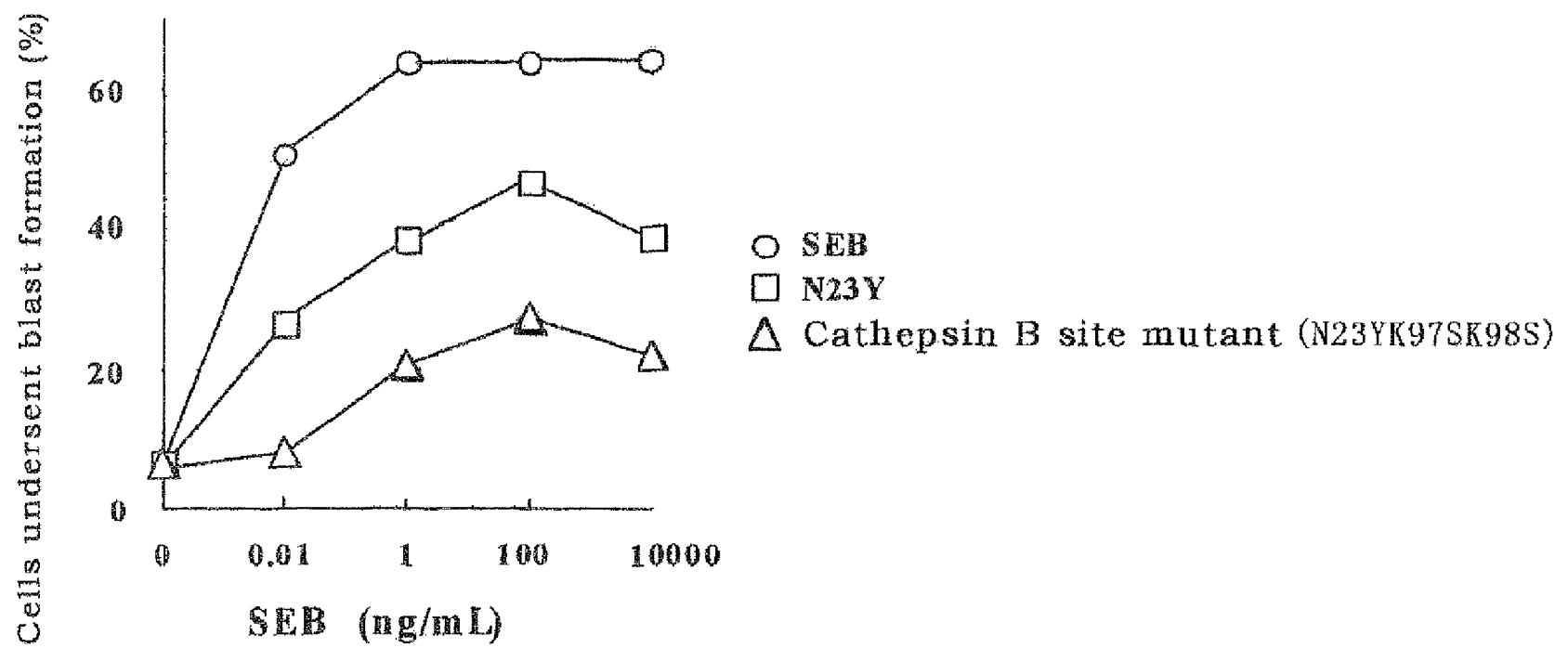

In addition, the PBMCs as described above were cultured in the presence of the same concentration of each of the modified SERs for 6 days and an extent of blast formation of T cells was investigated by FSC/SSC analysis of flow cytometry (hereinafter also referred to as "FACS"). As a result, N23Y induced significant blast formation to a little less than 40% of the cells at 1 ng/mL or more whereas the modified SEB N23YK97SK98S had a still reduced inducing activity, i.e. about ½ of N23Y (FIG. 5).

These results demonstrated that the modified SEB N23YK97SK98S had a proliferation-stimulating activity and a blast formation-inducing activity to human PBMCs in vitro that were extremely reduced as compared to those of wild type SEB.

Example 5

Assessment of Cytokine-inducing Activity of Modified SEB N23YK97SK98S

Figure 6:
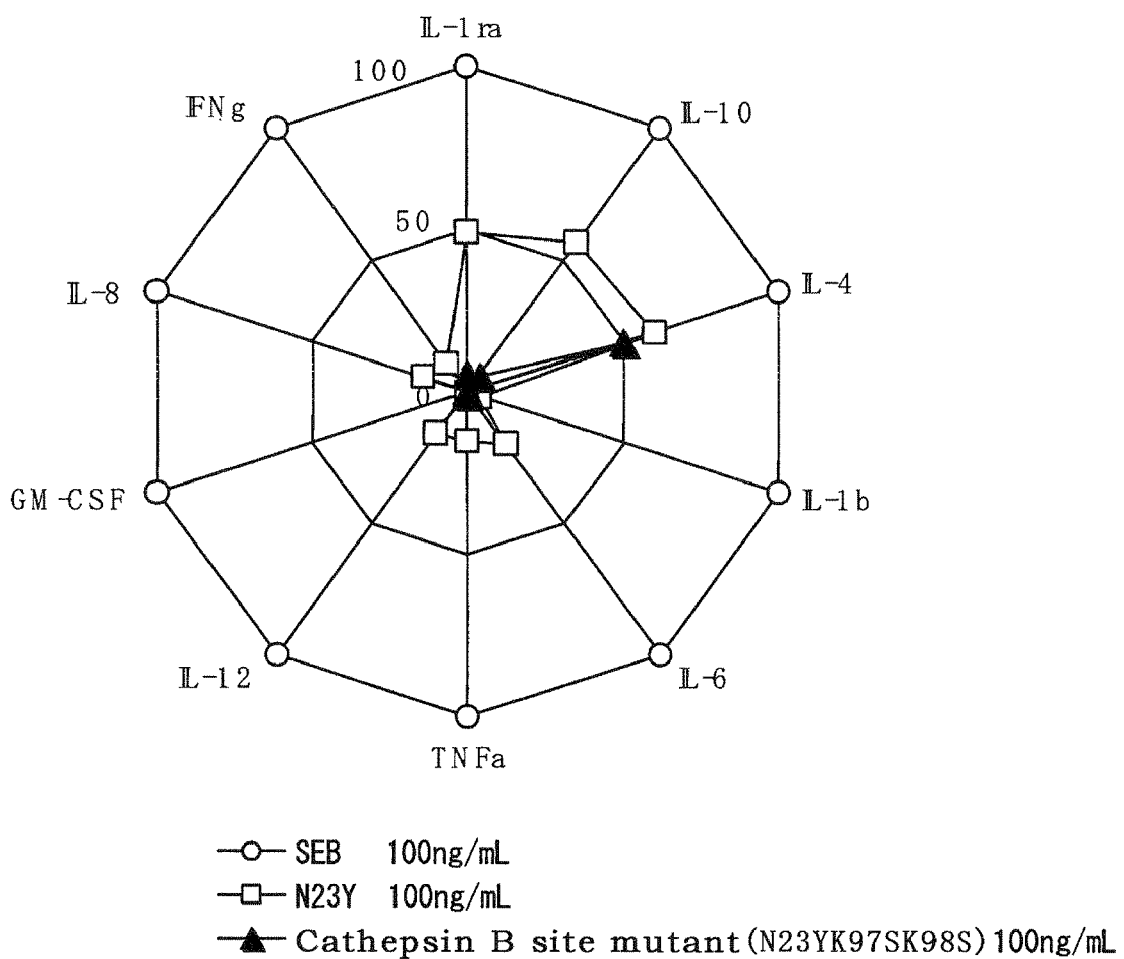
FIG. 6 is a graph showing a cytokine production-stimulating activity of the "N23YK97SK98S" modified SEB of the present invention in comparison with those of wild type SEB and of the "N23Y" modified SEB.

PBMCs from healthy adults were inoculated to a 24-well plate at $1 \times 10^6$ cells/mL and stimulated with SEB, the modified SEB N23Y or cathepsin B site mutant (N23YK97SK98S) at a concentration of each 100 ng/mL for 2 days to recover supernatant. Production of various cytokines (TNF-α, IL-1β, IL-6, IL-8, IL-12, IFN-γ, IL-1ra, IL-4, IL-10, GM-CSF) in the culture supernatant was determined with ELISA kit (CytoSets, CytoFix, ASAHI TECHNO GLASS CORPORATION). FIG. 5 shows a relative activity of the modified SEBs N23Y and N23YK97SK98S with a cytokine-inducing activity by stimulation with 100 ng/mL of SEB being 100%. As a result, it was found that the modified SEB N23YK97SK98S had an extremely reduced cytokine-inducing activity as compared to N23Y and SEB. In particular, production of inflammatory cytokines such as IL-UI, IL-6, TNF-α, IL-12, GM-CSF and IFN-γ was markedly reduced whereas production of an inhibitory cytokine such as IL-4 was maintained equivalent to that of N23Y (FIG. 6).

Example 6

Antibody Induction by Oral Administration of Modified SEB N23YK97SK98S

The modified SEBs N23Y and N23YK97SK98S were orally administered and whether an antibody is thereby induced was investigated.

Figure 7:
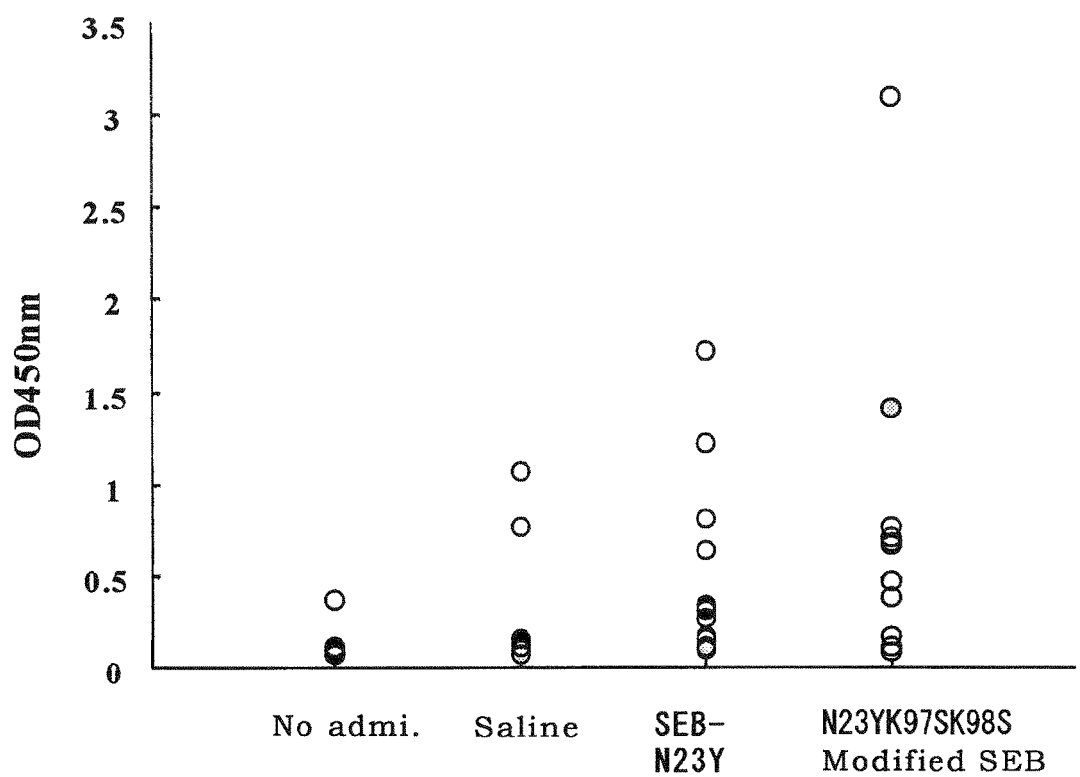
FIG. 7 is a graph showing induction of an anti-SEB antibody when the "N23YK97SK98S" modified SEB of the present invention is orally administered in comparison with that of the "N23Y" modified SEB.

They were orally administered with a probe at 10 μg/mouse every day for 4 weeks. When the test was completed, mice were totally bled and an antibody titer of an anti-SEB antibody in blood was determined by ELISA. As a result, it was demonstrated that many mice that received modified SEB N23YK97SK98S had an antibody titer of an anti-SEB antibody higher than that of the group of no administration or the control group of saline administration, indicating that oral administration of the modified SEB N23YK97SK98S could induce an anti-SEB antibody (FIG. 7).

INDUSTRIAL APPLICABILITY

The modified SEB of the present invention has resistance to a protease, especially trypsin and cathepsin B, and an extremely reduced toxicity as compared to the conventional modified SEBs. Therefore, the modified SEB of the present invention (modified SEB N23YK97SK98S) may efficaciously be used as a vaccine for prevention and treatment of opportunistic infections, severe diseases caused by a toxin produced by bacteria resistant to antibiotics and type I allergic disease.

The invention claimed is:

1. A modified Staphylococcal enterotoxin B (SEB) comprising the modified amino acid sequence of SEQ ID NO:1, wherein the lysines at positions 97 and 98 have been substituted with serines.

* * * * *

SEQUENCE LISTING

```
<160> NUMBER OF SEQ ID NOS: 8

<210> SEQ ID NO 1
<211> LENGTH: 239
<212> TYPE: PRT
<213> ORGANISM: Staphylococcus aureus

<400> SEQUENCE: 1

Glu Ser Gln Pro Asp Pro Lys Pro Asp Glu Leu His Lys Ser Ser Lys
 1               5                  10                  15

Phe Thr Gly Leu Met Glu Asn Met Lys Val Leu Tyr Asp Asp Asn His
             20                  25                  30

Val Ser Ala Ile Asn Val Lys Ser Ile Asp Gln Phe Leu Tyr Phe Asp
         35                  40                  45

Leu Ile Tyr Ser Ile Lys Asp Thr Lys Leu Gly Asn Tyr Asp Asn Val
     50                  55                  60

Arg Val Glu Phe Lys Asn Lys Asp Leu Ala Asp Lys Tyr Lys Asp Lys
 65                  70                  75                  80

Tyr Val Asp Val Phe Gly Ala Asn Tyr Tyr Tyr Gln Cys Tyr Phe Ser
                 85                  90                  95

Lys Lys Thr Asn Asp Ile Asn Ser His Gln Thr Asp Lys Arg Lys Thr
            100                 105                 110

Cys Met Tyr Gly Gly Val Thr Glu His Asn Ala Asn Gln Leu Asp Lys
        115                 120                 125

Tyr Arg Ser Ile Thr Val Arg Val Phe Glu Asp Gly Lys Asn Leu Leu
    130                 135                 140
```

-continued

```
Ser Phe Asp Val Gln Thr Asn Lys Lys Val Thr Ala Gln Glu Leu
145                 150                 155                 160

Asp Tyr Leu Thr Arg His Tyr Leu Val Lys Asn Lys Lys Leu Tyr Glu
                165                 170                 175

Phe Asn Asn Ser Pro Tyr Glu Thr Gly Tyr Ile Lys Phe Ile Glu Asn
                180                 185                 190

Glu Asn Ser Phe Trp Tyr Asp Met Met Pro Ala Pro Gly Asp Lys Phe
            195                 200                 205

Asp Gln Ser Lys Tyr Leu Met Met Tyr Asn Asp Asn Lys Met Val Asp
        210                 215                 220

Ser Lys Asp Val Lys Ile Glu Val Tyr Leu Thr Thr Lys Lys Lys
225                 230                 235
```

<210> SEQ ID NO 2
<211> LENGTH: 239
<212> TYPE: PRT
<213> ORGANISM: Staphylococcus aureus

<400> SEQUENCE: 2

```
Glu Ser Gln Pro Asp Pro Lys Pro Asp Glu Leu His Lys Ser Ser Lys
1               5                   10                  15

Phe Thr Gly Leu Met Glu Tyr Met Lys Val Leu Tyr Asp Asp Asn His
                20                  25                  30

Val Ser Ala Ile Asn Val Lys Ser Ile Asp Gln Phe Leu Tyr Phe Asp
            35                  40                  45

Leu Ile Tyr Ser Ile Lys Asp Thr Lys Leu Gly Asn Tyr Asp Asn Val
        50                  55                  60

Arg Val Glu Phe Lys Asn Lys Asp Leu Ala Asp Lys Tyr Lys Asp Lys
65                  70                  75                  80

Tyr Val Asp Val Phe Gly Ala Asn Tyr Tyr Tyr Gln Cys Tyr Phe Ser
                85                  90                  95

Ser Ser Thr Asn Asp Ile Asn Ser His Gln Thr Asp Lys Arg Lys Thr
            100                 105                 110

Cys Met Tyr Gly Gly Val Thr Glu His Asn Ala Asn Gln Leu Asp Lys
        115                 120                 125

Tyr Arg Ser Ile Thr Val Arg Val Phe Glu Asp Gly Lys Asn Leu Leu
130                 135                 140

Ser Phe Asp Val Gln Thr Asn Lys Lys Val Thr Ala Gln Glu Leu
145                 150                 155                 160

Asp Tyr Leu Thr Arg His Tyr Leu Val Lys Asn Lys Lys Leu Tyr Glu
                165                 170                 175

Phe Asn Asn Ser Pro Tyr Glu Thr Gly Tyr Ile Lys Phe Ile Glu Asn
                180                 185                 190

Glu Asn Ser Phe Trp Tyr Asp Met Met Pro Ala Pro Gly Asp Lys Phe
            195                 200                 205

Asp Gln Ser Lys Tyr Leu Met Met Tyr Asn Asp Asn Lys Met Val Asp
210                 215                 220

Ser Lys Asp Val Lys Ile Glu Val Tyr Leu Thr Thr Lys Lys Lys
                225                 230                 235
```

<210> SEQ ID NO 3
<211> LENGTH: 30
<212> TYPE: DNA
<213> ORGANISM: Artificial Sequence
<220> FEATURE:
<223> OTHER INFORMATION: Antisense primer designed for preparation of SEB variant by PCR amplification

```
<400> SEQUENCE: 3
aagtcgacaa tattagaaaa ggcaggtact                                           30

<210> SEQ ID NO 4
<211> LENGTH: 30
<212> TYPE: DNA
<213> ORGANISM: Artificial Sequence
<220> FEATURE:
<223> OTHER INFORMATION: Sense primer designed for preparation of SEB
      variant by PCR amplification

<400> SEQUENCE: 4
atgtcgactt aattgaatat ttaagattat                                           30

<210> SEQ ID NO 5
<211> LENGTH: 30
<212> TYPE: DNA
<213> ORGANISM: Artificial Sequence
<220> FEATURE:
<223> OTHER INFORMATION: Sense primer designed for preparation of SEB
      variant by PCR amplification

<400> SEQUENCE: 5
aagtcgacaa aaaatgtata agagattatt                                           30

<210> SEQ ID NO 6
<211> LENGTH: 30
<212> TYPE: DNA
<213> ORGANISM: Artificial Sequence
<220> FEATURE:
<223> OTHER INFORMATION: Antisense primer designed for preparation of
      SEB variant by PCR amplification

<400> SEQUENCE: 6
aagtcgactt tcactttttc tttgtcgtaa                                           30

<210> SEQ ID NO 7
<211> LENGTH: 42
<212> TYPE: DNA
<213> ORGANISM: Artificial Sequence
<220> FEATURE:
<223> OTHER INFORMATION: K97SK98S sense primer

<400> SEQUENCE: 7
caatgttatt tttctagcag cacgaatgat attaattcgc at                             42

<210> SEQ ID NO 8
<211> LENGTH: 42
<212> TYPE: DNA
<213> ORGANISM: Artificial Sequence
<220> FEATURE:
<223> OTHER INFORMATION: K97SK98S antisense primer

<400> SEQUENCE: 8
atgcgaatta atatcattcg tgctgctaga aaaataacat tg                             42
```